United States Patent [19]

Sims

[11] Patent Number: 4,694,956
[45] Date of Patent: Sep. 22, 1987

[54] DISPLAY RECEPTACLE FOR DECIDUOUS TEETH

[76] Inventor: Edward H. Sims, 521 North Chandler Avenue "B", Monterey Park, Calif. 91754

[21] Appl. No.: 928,388

[22] Filed: Nov. 7, 1986

[51] Int. Cl.$^4$ .................. A61K 19/10; B65D 85/00
[52] U.S. Cl. .................. 206/83; 206/63.5; 206/527; 206/822; 220/20; 220/23.83; 220/335; 433/229
[58] Field of Search .......... 206/83, 63.5, 822, 216, 206/581, 538, 1.7, 1.8, 525–527; 220/20, 23.2, 23.83, 335; 604/317; 433/49, 74, 77, 171, 229

[56] References Cited

U.S. PATENT DOCUMENTS

| | | | |
|---|---|---|---|
| 1,938,222 | 12/1933 | Green | 206/83 |
| 2,196,566 | 4/1940 | Sabattis | 206/83 |
| 2,375,645 | 5/1945 | Gordon | 206/83 |
| 2,620,919 | 12/1952 | Passmore | 206/83 |
| 2,874,487 | 2/1959 | Bloom et al. | 206/232 |
| 3,186,540 | 6/1965 | Breyer | 220/20 |
| 3,188,036 | 6/1965 | Sprung | 206/1.8 |
| 3,241,238 | 3/1966 | Kersten | 433/171 |
| 3,638,603 | 2/1972 | Conorer | 206/538 |
| 4,439,151 | 3/1984 | Whelan | 433/74 |

Primary Examiner—Stephen Marcus
Assistant Examiner—Brenda J. Ehrhardt
Attorney, Agent, or Firm—Christie, Parker & Hale

[57] ABSTRACT

Disclosed is a display receptacle for deciduous teeth in which transparent compartments for individual teeth are arranged in upper and lower arcuate rows along the facing rims of hingedly connected housing members. Each compartment opens to receive a particular tooth as it is lost by a child and is thereafter retained releasably closed. The main housing members are selectively spring biased to open or closed positions.

8 Claims, 5 Drawing Figures

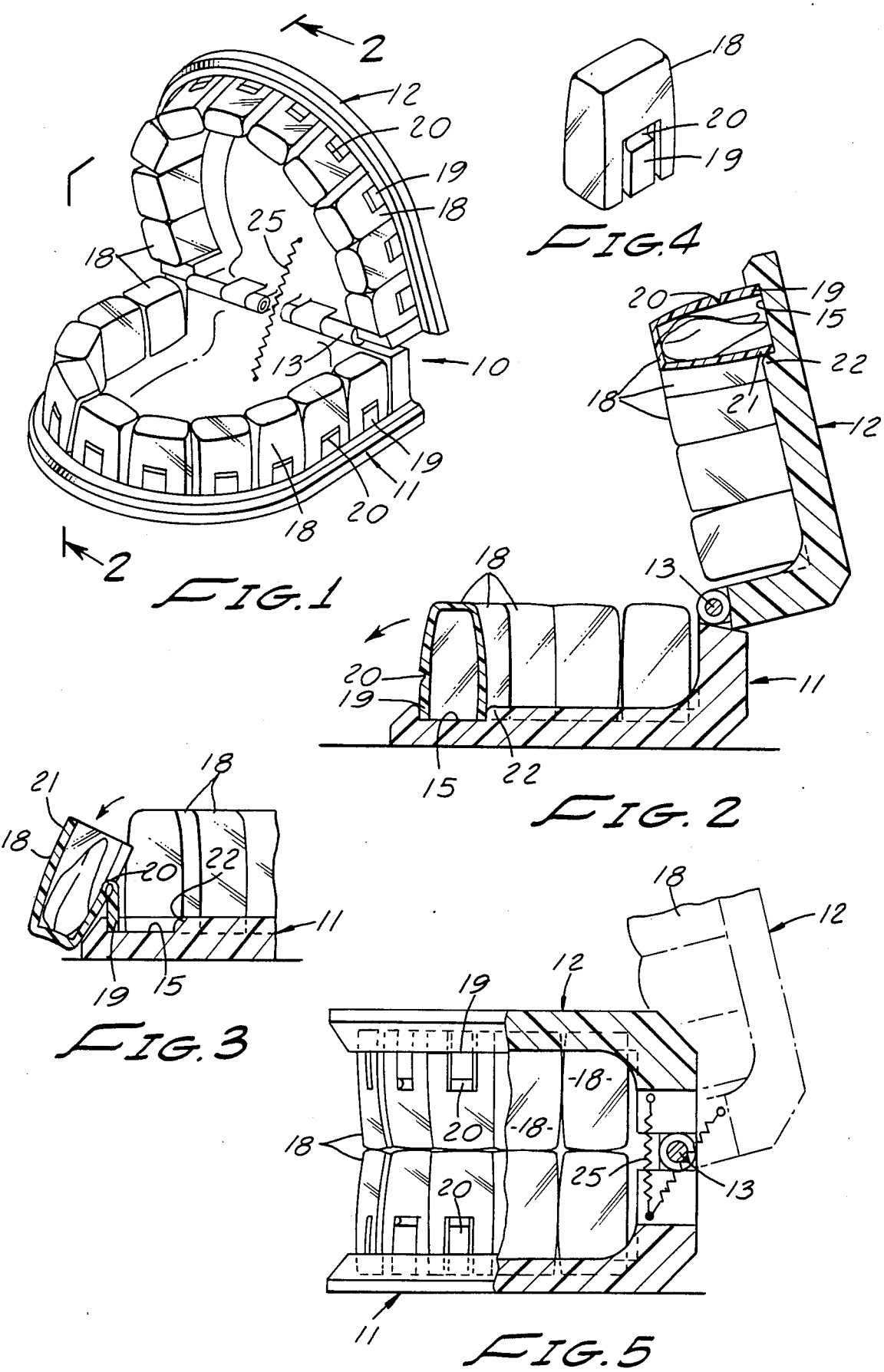

DISPLAY RECEPTACLE FOR DECIDUOUS TEETH

This invention relates to display receptacles, and more particularly to a unique receptacle in which superimposed U-shaped housing members support arcuate rows of compartments each receptive of an individual deciduous tooth for the edification of the donor.

BACKGROUND OF THE INVENTION

Satisfied by this invention is the need for an appropriate storage and display receptacle for the deciduous teeth of a child as successive ones of his primary teeth are lost. The storage compartments are preferably formed of transparent material in order that the teeth may be observed by the child and members of its family. Applicant has conducted an investigation but has not found any prior provision to meet this need.

SUMMARY OF THE INVENTION

In view of the foregoing there is provided by this invention an inexpensive, attractive, practical receptacle for storing and displaying a particular child's deciduous teeth as they are lost. The receptacle has upper and lower U-shaped members hingedly interconnected and provided along their facing rims with rows of transparent compartments each accommodating a particular tooth. The housing members are spring biased to either a normal closed position with the tooth compartments of the two rows in contact with one another or in an open position providing access to each tooth compartment. To avoid loss each tooth compartment is hingedly connected to one of the housing members.

Accodingly, it is a primary object of the present invention to provide a simple and attractive storage and display receptacle for deciduous teeth.

Another object of the invention is the provision of deciduous tooth receptacle simulating the upper and lower gum supporting arches of a person's mouth and provided with individual transparent compartments for each deciduous tooth.

These and other more specific objects will appear upon reading the following specification and claims and upon considering in connection therewith the attached drawing to which they relate.

Referring now to the drawing in which a preferred embodiment of the invention is illustrated:

FIG. 1 is a perspective view of an illustrative embodiment of the invention showing a receptacle cover in its stable open position;

FIG. 2 is a cross sectional view taken along line 2—2 on FIG. 1;

FIG. 3 is a fragmentary cross sectional view showing one of the tooth receptacles in open position to receive a deciduous tooth; and FIG. 4 is a perspective view of a single tooth receptacle before its hinge is attached to one of the cover members; and FIG. 5 is a side elevational view with portions of the rear half of the closed receptacle cut away to show hinge details of the main receptacle.

Referring initially more particularly to FIG. 1 there is shown a deciduous tooth display receptacle designated generally 10 having upper and lower generally U-shaped housing members 11 12 hingedly interconnected by hinge 13 transversely of their rear ends. As is best shown in FIGS. 2 and 5, hinge 13 is located midway between the lower and upper members 11, 12. Extending along and slightly inwardly of the arcuate edges of the housing member is a shallow arcuate groove 15 along which rows of separate tooth receptacles 18 are arranged, there being a separate receptacle for each deciduous tooth.

Tooth receptacles 18 are preferably formed of transparent plastic material with a portion 19 of the outer rim of each bonded or otherwise fixedly secured to the outer rim portion of groove 15. To be noted is the fact that lip portion 19 includes an itegral live hinge 20 best shown in FIG. 3 thereby permitting each tooth compartment 18 to be pivoted from the closed position shown in FIG. 1 to the open tooth receiving position shown in FIG. 3. The inner transverse rim edge 21 of each tooth compartment preferably has a slight interference or a frictional fit with the inner sidewall 22 of groove 15. This arrangement serves to maintain the individual tooth compartments 18 releasably closed until an individual one is deliberately pressed toward its open position. This guards against accidental opening of tooth compartments containing teeth when either of the closure members 11, 12 are open.

As is best shown in FIG. 5, the main housing members 11 and 12 include a tension spring 25 having its opposite ends anchored to the housing members as best shown in FIG. 5. The center line of this spring is disposed forwardly of hinge 13 when the housing members are closed and is disposed rearwardly thereof when the housing members are open and thereby effective to hold these members open or closed. It will be noted from FIG. 2 that the extreme open position is shown in FIGS. 1 and 2 with portions of the two housing members in contact with one another to arrest opening movement.

Principal components of the invention receptacle are preferably formed of molded plastic material. The housing members may be in color but the tooth receptacles 18 are preferably formed of transparent material in order that their contents will be viewable at all times.

The use of the described and illustrated deciduous tooth receptacle will be quite apparent from the foregoing detailed description. Each time a child looses a primary tooth it is proudly displayed in the appropriate one of compartments 18 simply by opening the main housing to the position shown in FIG. 2 and then opening the appropriate one of receptacles 18 as shown in FIG. 3 to receive the tooth. Thereafter, the receptacle is closed and retained snugly in this position by the interference fit of its lip 21 with groove sidewall 22. Thereafter the main housing members are restored to the closed position and retained there by the automatic action of tension spring 25.

While the particular display receptacle for deciduous teeth herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A display receptacle for deciduous teeth comprising:

spaced apart upper and lower generally U-shaped members movable connected together crosswise of their generally straight transverse rear perimeters; and an arcuate row of tooth-like receptacles connected along the facing rim edge portions of said upper and lower members each adapted to receive and store a deciduous tooth and each including hinge means connecting the same to a respective one of said upper and lower members.

2. A display receptacle as defined in claim 2 characterized in the provision of hinge means pivotably interconnecting said upper and lower members on an axis generally midway between the remote exterior surfaces thereof.

3. A display receptacle as defined in claim 2 characterized in the provision of spring means between said upper and lower members normally operable to hold said upper and lower members in a closed position with said rows of tooth-like receptacles closed and substantially in contact with one another.

4. A display receptacle as defined in claim 3 characterized in that said spring means is arranged to hold said upper and lower members selectively closed and in an open position when said members are pivoted apart beyond a predetermined open position.

5. A display receptacle as defined in claim 1 characterized in that said upper and lower members and said tooth-like receptacles are formed of plastic material.

6. A display receptacle as defined in claim 5 characterized in that said tooth-like receptacles are formed of transparent plastic material.

7. A display receptacle as defined in claim 5 characterized in that said hinge means for said tooth-like receptacles comprises a live hinge located on the outwardly facing sides thereof.

8. A display receptacle as defined in claim 7 characterized in that said rows of tooth-like receptacles open into a shallow arcuate groove along the facing rim portions of said upper and lower members; means anchoring the outer edges of said rows of tooth-like receptacles to the juxtaposed edge of a respective one of said grooves; and the opposite inner rim edges of said tooth-like receptacles normally having an interference fit with the juxtaposed inner sidewall of said shallow groove and effective to hold said tooth-like receptacles closed until deliberately released by an outward pivotal movement.

* * * * *